United States Patent
Turjak

[11] Patent Number: 5,769,103
[45] Date of Patent: Jun. 23, 1998

[54] FLAT INTERDENTAL SPACE CLEANER

[76] Inventor: Visnja Turjak, Aleja pomoraca 23, Zagreb, Croatia, 10020

[21] Appl. No.: 710,895

[22] Filed: Sep. 23, 1996

[30] Foreign Application Priority Data

Sep. 22, 1995 [HR] Croatia ................................ 950495 A

[51] Int. Cl.⁶ .................................................. A61C 15/02
[52] U.S. Cl. .......................................................... 132/329
[58] Field of Search .................................... 132/329, 321, 132/323, 328; 433/39; D28/64

[56] References Cited

U.S. PATENT DOCUMENTS 3,771,537 11/1973 Schole .
4,377,381 3/1983 Westman ................................ 132/321

FOREIGN PATENT DOCUMENTS 1 755 702 10/1953 Germany .
67 50 489 1/1969 Germany .
89 07 895 11/1989 Germany .
671331 8/1989 Switzerland .
2 059 266 4/1981 United Kingdom .
2 209 283 5/1989 United Kingdom .

*Primary Examiner*—Todd E. Manahan
*Assistant Examiner*—E. Robert
*Attorney, Agent, or Firm*—Jacobson, Price, Holman & Stern, PLLC

[57] ABSTRACT

A flat interdental space cleaner includes an essentially flat resilient strip. The free end portions of the flat resilient strip are provided with an essentially uniform thickness and a width comparable to the visible length of teeth. This enables passing between two teeth into the interdental space, allowing an easy and successful removal of food residues and soft sediments or plaque from the surface of teeth, in particular from interdental spaces or pariodontal pockets. An easy and discreet handling of interdental space cleaning is provided on any occasion.

9 Claims, 2 Drawing Sheets

FLAT INTERDENTAL SPACE CLEANER

FIELD OF THE INVENTION

The present invention refers globally to a device for maintaining of dental hygiene and more particularly to a flat interdental space cleaner.

BACKGROUND OF THE INVENTION

For maintaining of dental hygiene the regular and correct use of a toothbrush is one of the essential necessities. However, the interdental spaces are normally inaccessible to a toothbrush and therefore commonly prone to caries and inflammation of the gum. As inflammation proceeds it leads eventually to damage of the periodontium, the creation of pockets between the teeth, receding gums, loose teeth and finally the loss of teeth.

For removing food residues and soft sediments or plaque from the interdental spaces or pariodontal pockets the use of a toothbrush normally is not sufficient. For cleaning interdental spaces the most commonly used device is a toothpick. Such toothpick normally shows a sharpened or rounded edge and is of a rod-like configuration generally showing the following disadvantages: It cannot pass between the teeth with narrow interdental spaces, it is not resilient and therefore often breaks, it is normally useless for the back teeth, which are not easily accessible, and there always remains the possibility of injury. For avoiding several of these disadvantages of known toothpicks there is for example proposed in CH-A 671 331 a toothpick consisting of a flexible blade, which can be slid into or out of a sheath by a notched projection on one side of the blade engaging with a slot along one side of the sheath. Such construction is comparable to knives, which can be hidden and protected in special coverings and furthermore this known construction of a toothpick is provided with a saw-like edge resulting in damages of the surface layer of the teeth or injuries of the gum.

Besides the use of toothpicks, dental floss is often recognized as the most useful device for cleaning interdental spaces. Nevertheless, its usage is often unpopular because it is necessary to be familiar with the application technique which requires time, patience and the use of both hands in front of a mirror. Furthermore an interdental brush can be used only in the case of wider interdental spaces and its application also requires a mirror.

SUMMARY OF THE PRESENT INVENTION

The present invention therefore aims at providing an improved device for maintaining of dental hygiene in the form of a flat interdental space cleaner allowing an easy and successful removal of food residues and soft sediments or plaque from the surface of teeth, in particular from interdental spaces or pariodontal pockets, without any additional auxiliary means, such as mirrors, and allowing an easy and discreet handling of any occasion. For solving these problems the flat interdental space cleaner according to the present invention comprises an essentially flat resilient strip wherein the free end portions of the flat resilient strip are provided with an essentially uniform thickness and a width comparable to the visible length of teeth enabling passing between two teeth into the interdental space. Because of the fact that the flat interdental space cleaner according to the present invention comprises an essentially flat resilient strip, wherein the free end portions of the flat resilient strip are provided with an essentially uniform thickness, it is easily possible that these free end portions pass between the teeth owing to the thickness and elasticity of the free end portions of the flat resilient strip being the functional parts of the device according to the invention. Merely by the passage of the free end portions, the surface of the teeth in contact is cleaned, and as it enters into the interdental space or gap, if present, its simple movement removes food residues and plaque from that area. An effective removal of dirt from a tooth surface in contact with a neighboring tooth and from the bottom of the interdental space or pocket is further assisted by the fact that the width of the elastic strip of the flat interdental space cleaner according to the present invention is comparable to the visible length of teeth to be cleaned. The length of the flat elastic strip can be about 6 cm, which allows a discreet application hiding the inventive cleaner in the hand of the user, where at the same time the flat resilient strip with the free end portions of an essentially uniform thickness allows easy access into the interdental spaces not only of the front teeth, but also of the back teeth, which are normally not easily accessible.

For further simplifying the use of the flat interdental space cleaner of the present invention it is proposed that the flat resilient strip comprises a curved, bent or angled configuration. Such a curved, bent or angled configuration, for example showing the contures of a boomerang, allows easy handling of the flat interdental space cleaner regardless of the teeth to be cleaned.

For allowing an easy and successful insertion of the flat interdental space cleaner also into relatively narrow gaps or narrow interdental spaces according to a further preferred embodiment it is proposed that the free ends of the resilient strip comprise a uniform thickness of below 0,1 mm, preferably between 0,03 and 0,05 mm. Such a thickness of the functional parts or the free end portions of the flat resilient strip allow a passage between teeth at the contact point and to insert the functional parts into the interdental spaces or a pocket whereas at the same time providing a sufficient stability and flexibility for using the flat interdental space cleaner according to the present invention without any risks of breakage or damage of the cleaning device and thereby avoiding any risks of injuries.

For allowing an easy use of a flat interdental space cleaner according to the present invention also for different gaps or spaces between neighboring teeth it is further preferred that the free ends are provided with different uniform thicknesses. Such a configuration, wherein the two free ends or the functional parts of the flat resilient strip are provided with different uniform thicknesses allow an effective use and a succesfull cleaning of different forms of interdental spaces or pariodontal pockets.

For minimizing a potential risk of injuries it is further preferred that the free ends of the flat resilient strip are provided with rounded edges. Such rounded edges of the free ends of the flat resilient strip furthermore allow an easy insertion or passage through the space between neighboring teeth.

With deepened interdental spaces or pockets, which might be created as a result of an inflammation caused by insufficient cleaning of those spaces, there might exist problems of reaching the inner ends of such pariodontal pockets with the functional parts or free ends of the flat resilient strip showing a uniform width besides the uniform thickness. For simplifying the cleaning of such deep pariodontal pockets it is therefore preferably proposed that the free ends are provided with essentially circular protrusions forming rounded edges with a diameter being greater than the width of adjacent areas of the resilient strip with an essentially uniform width. Such essentially circular protrusions being greater than the width of adjacent areas of the elastic strip allow an easier and deeper insertion into any interdental spaces to be cleaned by the flat interdental space cleaner.

As it was indicated above, at least the free ends or functional parts of the resilient strip are to be provided with a relatively small uniform thickness for allowing an easy insertion into or passage through interdental spaces between neighboring teeth. If the flat elastic strip would be provided with such small thickness over its total length, it can be understood that such thin resilient strip could cause problems when handling the flat interdental space cleaner according to the present invention. Furthermore it might involve great expenses to produce the flat resilient strip with different thicknesses for the free ends and its middle portion for giving a sufficient mechanical strength and for allowing an easy handling. Therefore according to a further preferred embodiment of the present invention the flat resilient strip is enveloped by a cover in its middle portion leaving the free ends protruding from the cover. Such a cover, covering only the middle portion of the flat resilient strip might be made of sufficently strong and resistant material to provide the flat interdental space cleaner with a sufficient stability and strength for allowing an easy handling and for ensuring an easy protection of the flat resilient strip. Such a cover might preferably be made of metal or plastics and furthermore could be provided for example with anatomical or ergonomic gripping or handling elements allowing an easy handling. Furthermore the flat interdental space cleaner according to the present invention could be provided with special design elements, if necessary, without hindering the effective use of the flat interdental space cleaner by leaving the free end portions or functional parts protruding from the cover.

According to a further preferred embodiment the flat resilient strip is made of metal, in particular stainless steel, or chemically inert plastics, thereby allowing a cheap and easy production of the flat interdental space cleaner and in particular the flat resilient strip and furthermore allowing the usage of materials which enable a repeated use of the flat interdental space cleaner after cleaning the flat resilient strip with a suitable disinfectant.

BRIEF DESCRIPTION OF THE DRAWINGS

The present invention is further explained with regard to the enclosed drawing showing schematical representations of different examples of flat interdental space cleaners according to the present invention, wherein.

DETAILED DESCRIPTION OF THE PREFERRED EMBODIMENTS

Figure 1:
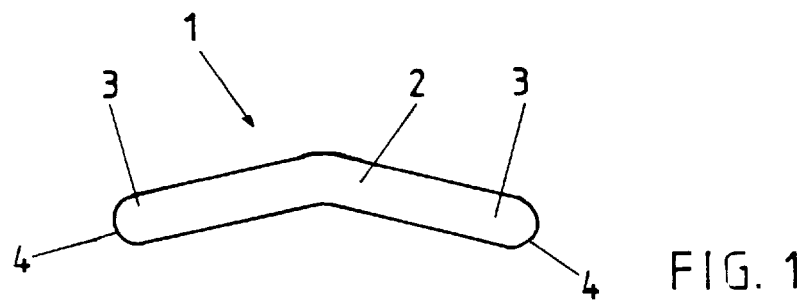
FIG. 1 shows an elevational view of a first embodiment of the flat interdental space cleaner according to the present invention, wherein the flat resilient strip is provided with an essentially uniform width over its whole length.
Figure 2:
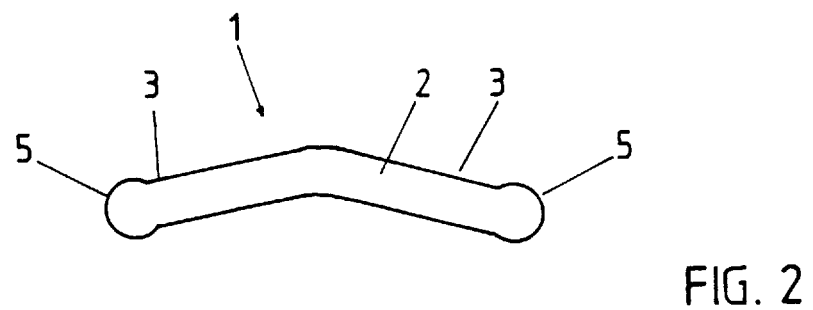
FIG. 2 shows an elevational view of a modified embodiment of a flat interdental space cleaner according to the present invention, wherein the free ends are provided with essentially circular protrusions enabling the entry into a deeper interdental space or pocket.

In FIGS. 1 and 2 a flat interdental space cleaner, generally indicated with 1, comprises an essentially flat resilient strip 2 with an angled or curved configuration, for example like a boomerang. The free ends 3 being the functional part of the flat interdental space cleaner 1 are provided with an essentially uniform thickness as can be gathered for example from FIGS. 5 and 6. Furthermore the free ends 3 are provided with rounded edges 4 in the embodiment of FIG. 1, whereas in FIG. 2 the free ends 3 are provided with essentially circular protrusions 5, which also define rounded edges and whose diameter is larger than the width of the adjacent areas of the flat resilient strip 2 or the free ends 3 thereof. The embodiment shown in FIG. 2 is essentially useful when cleaning very deep interdental spaces or pariodontal pockets.

Figure 3:
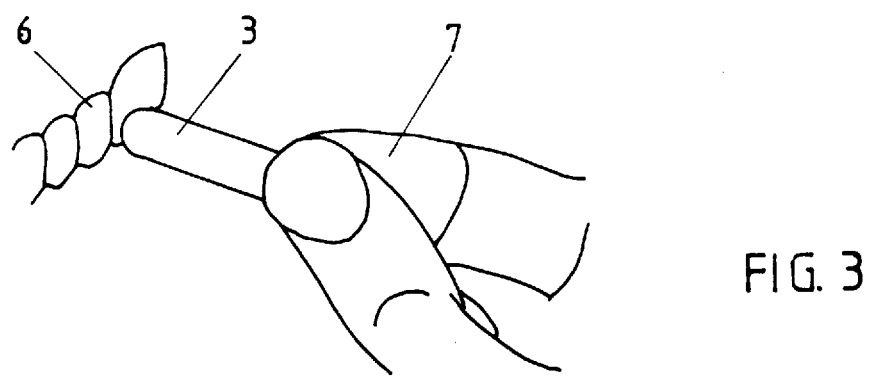
FIG. 3 shows a perspective view of the application of a flat interdental space cleaner according to the present invention.

In FIG. 3 the use of a flat interdental space cleaner 1 is schematically shown. The flat interdental space cleaner 1 is held in its middle portion and one free end, for example as shown in FIG. 1, will be inserted into the interdental spaces between neighboring teeth, which are schematically indicated with 6 in FIG. 3. As can be easily understood, the flat interdental space cleaner can be easily held by fingers 7 and because of its short length, and in particular its bent configuration, can also be easily concealed in the hand allowing an easy handling and use on practically any occasion.

Figure 4:
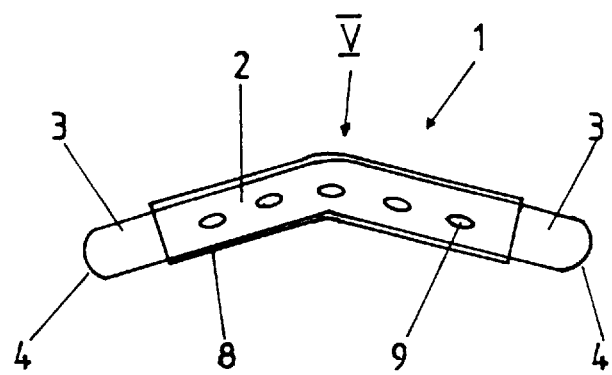
FIG. 4 shows an elevational view of a further modified embodiment of a flat interdental space cleaner according to the present invention, wherein the middle portion of the flat resilient strip is enveloped by a cover.
Figure 5:
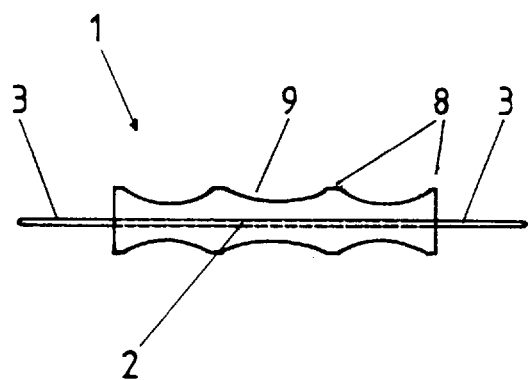
FIG. 5 is a front view according to arrow V of FIG. 4.

The embodiment shown in FIGS. 4 and 5 once more comprises a flat resilient strip 2, wherein the middle portion is envelopped by a cover 8, from which the free ends 3 or the functional parts of the flat interdental space cleaner 1 protrude for a sufficient length for allowing an easy and successfull cleaning of interdental spaces. The cover 8 might be produced of sufficiently resistant and strong material for providing an enhanced strength to the flat interdental space cleaner 1, whose flat resilient strip 2 is provided with a uniform thickness over its total length, as can be seen in particular from FIG. 5. Furthermore the cover 8 might be provided with special design or gripping elements, generally indicated with 9.

Figure 6:
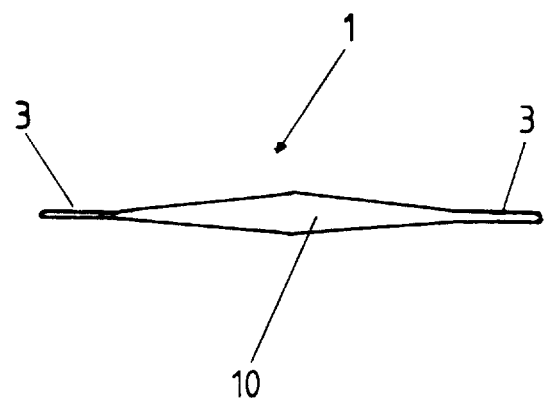
FIG. 6 is another front view of a further modified embodiment of a flat interdental space cleaner according to the present invention, wherein the flat resilient strip is provided in its middle portion with a thickened area for allowing a greater stability and strength without any additional cover or reinforcement means being necessary.

Whereas in the embodiment of FIGS. 4 and 5 the flat resilient strip 2 is provided with an essentially uniform thickness over its total length, in the embodiment shown in FIG. 6 the flat resilient strip 2 is provided with relatively thin free ends 3, whereas its middle portion 10 is provided with a greater thickness for allowing a sufficient stability of the total flat interdental space cleaner 1 without any cover. Furthermore it can been seen from FIG. 6, that the free ends 3 on both sides of the middle portion 10 are provided with different thicknesses allowing an easy and successful cleaning of gaps with different width.

The embodiment shown in FIG. 6, wherein the free ends 3 of the flat resilient strip 2 and the middle portion 10 showing a greater thickness are made from one piece, can for example be produced of any suitable and preferably chemically inert and physiologically acceptable plastic material, whereas a flat elastic strip shown in FIGS. 4 and 5 can for example be made of a suitable metal, in particular stainless steel, being covered by a cover 8, for example produced of any suitable plastic material.

It is to be understood that the relative thickness of the free ends 3 or the functional parts of the flat interdental space cleaner 1 is shown on an exaggerated scale, particularly in FIGS. 5 and 6, and in practice should be lower than 0,1 mm and in particular between 0,03 and 0,05 mm for allowing an easy insertion into interdental spaces or pockets or passage through interdental spaces. Furthermore the surface of the free ends 3 might be provided with a certain roughness or corrugations allowing an enhanced cleaning effect, when moving the free ends 3 through interdental spaces, in particular for loosening and removing plaque.

I claim:

1. Flat interdental space cleaner comprising an essentially flat resilient strip in an angled configuration so as to be substantially boomerang shaped, and free end portions of flat resilient strip including different uniform thicknesses and a width comparable to a visible length of teeth for enabling passing between two teeth into the interdental space.

2. Flat interdental space cleaner according to claim 1, wherein the free ends of the resilient strip comprise a uniform thickness of below 0.1 mm.

3. Flat interdental space cleaner according to claim 2, wherein the free ends of the resilient strip comprise a uniform thickness of between 0.03 and 0.05 mm.

4. Flat interdental space cleaner according to claim 1, wherein the free ends of the flat resilient strip are provided with rounded edges.

5. Flat interdental space cleaner according to claim 1, wherein the free ends are provided with essentially circular protrusions forming rounded edges with a diameter being greater than the width of adjacent areas of the resilient strip.

6. Flat interdental space cleaner according to claim 1, wherein the flat resilient strip is enveloped by a cover in its middle portion leaving the free ends protruding from the cover.

7. Flat interdental space cleaner according to claim 6, wherein the cover is made of metal or plastics.

8. Flat interdental space cleaner according to claim 1, wherein the flat resilient strip is made of one of metal and chemically inert plastics.

9. Flat interdental space cleaner according to claim 8, wherein the flat resilient strip is made of stainless steel.

\* \* \* \* \*